United States Patent
DuBois

(10) Patent No.: US 7,307,124 B2
(45) Date of Patent: Dec. 11, 2007

(54) HOT-MELT ADHESIVE COMPOSITION FOR NON-WOVENS

(75) Inventor: Donn A. DuBois, Houston, TX (US)

(73) Assignee: Kraton Polymers U.S. LLC, Houston, TX (US)

( * ) Notice: Subject to any disclaimer, the term of this patent is extended or adjusted under 35 U.S.C. 154(b) by 340 days.

(21) Appl. No.: 11/049,097

(22) Filed: Feb. 2, 2005

(65) Prior Publication Data

US 2005/0187343 A1 Aug. 25, 2005

(51) Int. Cl.
C08F 297/04 (2006.01)

(52) U.S. Cl. .......................... 525/98; 525/99; 525/88; 525/89; 525/314; 525/316; 524/505; 524/499; 524/474

(58) Field of Classification Search .................. 525/98, 525/99, 88, 89, 314, 316; 524/505, 499, 524/474
See application file for complete search history.

(56) References Cited

U.S. PATENT DOCUMENTS

| | | | |
|---|---|---|---|
| 4,120,915 A | | 10/1978 | Fodor et al. |
| 5,292,819 A | * | 3/1994 | Diehl et al. ................. 525/314 |
| 5,399,627 A | | 3/1995 | Diehl et al. |
| 5,916,959 A | * | 6/1999 | Lindquist et al. ........... 524/505 |
| 6,462,137 B2 | * | 10/2002 | Li et al. ....................... 525/314 |
| 6,833,411 B2 | | 12/2004 | Fujiwara et al. |
| 2002/0120069 A1 | | 8/2002 | Li et al. |
| 2003/0232928 A1 | | 12/2003 | Atwood et al. |
| 2004/0116582 A1 | | 6/2004 | De Keyzer et al. |
| 2005/0137312 A1 | | 6/2005 | DuBois |

FOREIGN PATENT DOCUMENTS

| | | |
|---|---|---|
| EP | 0 532 831 A1 | 3/1993 |
| EP | 0 588 923 B1 | 3/1994 |
| EP | 0 669 350 A1 | 8/1995 |
| EP | 0 802 251 A1 | 10/1997 |
| EP | 1 426 411 A1 | 6/2004 |
| EP | 1 493 790 A1 | 1/2005 |
| EP | 1 566 423 | 8/2005 |
| JP | 2004-131707 | 4/2004 |
| WO | 91/02039 | 2/1991 |
| WO | 2004/074394 A1 | 9/2004 |
| WO | 2004074394 A1 | 9/2004 |
| WO | 2004/097523 | 11/2004 |
| WO | 2005/063914 A2 | 7/2005 |
| WO | 20050063914 A2 | 7/2005 |

OTHER PUBLICATIONS

K. Lee, et al. *Synthesis and Tensile Properties of Styrene-Butadiene-Isoprene Ternary Block Copolymer; International Union of Pure Applied Chemistry*; Jun. 30-Jul. 4, 2003. p. O48.

* cited by examiner

Primary Examiner—James J. Seidleck
Assistant Examiner—Olga Asinovsky
(74) Attorney, Agent, or Firm—Donna Blalock Holguin

(57) ABSTRACT

Hot-melt adhesive compositions used in non-woven assemblies, comprising:
(a) 100 parts by weight of a block copolymer of the formula S-(I/B)-S, wherein S represents a predominantly poly(styrene) block and (I/B) represents a polymer block obtained by at random copolymerization of a mixture of predominantly isoprene and butadiene in a weight ratio in the range of from 70:30 to 30:70, wherein the total block copolymer has a melt flow index measured at 200° C./5 kg in the range of from 0.1 to 12 g/10 min. and has a poly(styrene) content of from 28 to 50 wt % and a coupling efficiency of from 50 to 100%,
(b) from 250 to 300 parts by weight of a tackifying resin,
(c) from 50 to 150 parts by weight of a plasticizer, and
(d) from 0 to 3 parts by weight of auxiliaries, such as stabilizers and/or antioxidants,
and disposable articles, comprising at least a non-woven element and assembled by the use of said hot-melt adhesive compositions.

20 Claims, No Drawings

HOT-MELT ADHESIVE COMPOSITION FOR NON-WOVENS

FIELD OF THE INVENTION

The present invention relates to hot-melt adhesive compositions for non-wovens. More particularly, the present invention relates to hot-melt adhesive compositions for the manufacture of sanitary articles such as infant and adult diapers, sanitary napkins, incontinent pads, bed pads, feminine pads, panty shields, and the like, comprising at least one element of non-woven material, and also to block copolymers to be used therein.

BACKGROUND

It is generally known in the art, as taught in WO 9102039, EP 0532831A and EP 0802251A, that block copolymers comprising terminal poly(styrene) blocks and one or more central poly(isoprene) blocks, more particularly triblock copolymers, are used in hot melt adhesive compositions for the manufacture of disposable articles. More specifically triblock copolymers having a poly(styrene) content of from 25 to 35 wt % and having a total apparent molecular weight of from 140,000 to 145,000 (e.g., KRATON® D-1165 block copolymer) are used in hot-melt adhesive compositions in the diaper industry in two manners:

1. as assembly adhesive to glue the diaper poly(ethylene) main frame and
2. as an attachment adhesive to glue the elastic attachments which are used as waist and leg bands.

Such adhesives must be lightly colored, transparent, low in odor, sprayable at 300° F., show good adhesion to poly(olefin) films and not strike through the non-woven back sheet. They must also be relatively inexpensive.

Elastic attachment adhesive is used to adhere elastic threads to polyethylene and non-woven films in order to form an elastic waist or leg band. Multiple strands of elastic threads are elongated, commonly 300%, and coated with adhesive composition at a temperature of about 300° F. just prior to being pinched inside of the poly(olefin) and non-woven webs. Like construction adhesives, they are usually sprayed in a spiral pattern. When the ends of the elastic are cut later in the process, the composite contracts causing the non-woven and poly(olefin) films to pucker to form an elastic band.

Although block copolymers such as KRATON D-1165 block copolymer show an acceptable hot-melt viscosity/temperature profile and have a sufficiently low viscosity at the usually applied hot-melt temperatures of up to 320° F. thereby enabling efficient processing, there is still an economic need for more block copolymers which demonstrate processing efficiency, in combination with other attractive properties noted hereinbefore.

It will be appreciated that a relatively low hot-melt viscosity facilitates a high production speed in a diaper manufacturing line without the production of significant amounts of off spec product. Problems which normally cause such off spec product may be, for example, adhesive viscosity degradation, adhesive discoloration, damage to the polyethylene film or formation or char. Accordingly, developmental efforts in diaper manufacture continue today.

Therefore, it is an object of the present invention to provide improved adhesive compositions which show a reasonable viscosity at temperatures in the range of from about 280° F. to about 320° F. in order to avoid the hereinbefore mentioned problems while allowing sprayability.

Another object of the present invention is the formation of sanitary articles comprising at least one non-woven layer and manufactured using said improved hot-melt adhesive compositions.

As a result of extensive research and experimentation it has now surprisingly been found that radial block copolymers comprising terminal, predominantly poly(styrene) blocks and central (I/B) blocks, afford a good sprayable hot-melt viscosity at the temperatures preferably applied in the diaper industry, i.e. in the range of from about 280 to about 320° F. In addition, these radial polymers afford excellent color stability, superior adhesive performance and better viscosity stability compared to conventional adhesive compositions based on S-I-S block copolymer.

Moreover, hot melt adhesive compositions comprising said S-(I/B) blocks containing block copolymers have been found to show an increased cohesion.

SUMMARY OF THE INVENTION

The present invention relates to a hot melt adhesive composition used in non-woven assemblies, comprising:

(a) 100 parts by weight of a block copolymer of the formula $[S-(I/B)]_nX$, wherein S represents a predominantly poly(styrene) block and (I/B) represents a polymer block obtained by at random copolymerization of a mixture of predominantly isoprene and butadiene in a weight ratio in the range of from about 70:30 to about 30:70, wherein n is an integer in the range of from 3 to 5, preferably from 3 to 4, and wherein X is the remainder of a coupling agent, wherein the block copolymer has a poly(styrene) content of from about 28 to about 50 wt %, a coupling efficiency of from about 50 to about 100% and a melt flow index measured at 200° C./5 kg, ranging from about 1.0 to about 12 g/10 min, (b) from 250 to 300 parts by weight of a tackifying resin,
(c) from 50 to 150 parts by weight of a plasticizer, and
(d) optionally from 0 to 3 parts by weight of stabilizers and/or antioxidants.

Other aspects of the present invention are formed by disposable articles such as infant and adult diapers, sanitary napkins, incontinent pads, bed pads, feminine pads, panty shields, comprising at least one non-woven element and assembled using the hereinbefore specified hot melt adhesive compositions, and by the specific block copolymers to be used therein.

The adhesive compositions of the present invention are useful for applications such as disposable diapers, feminine protection articles, incontinent pads, bed pads, surgical drapes and gowns, and similar articles. The inventive radial, mixed-midblock polymers have been shown to have good spayability, even at surprisingly high viscosities. Other features compared to convention SIS —based non-wovens adhesives include improved viscosity stability, improved color stability when heat-aged and good creep resistance for elastic fiber attachment formulations.

DETAILED DESCRIPTION OF THE INVENTION

The main components used in the adhesive compositions of the present invention are a block copolymer (component (a)), a tackifying resin (component (b)), a plasticizer (component (c)) and optionally, stabilizers or antioxidants (component (d)).

The block copolymer of the present invention is represented by a structure of the general formula $[S-(I/B)]_nX$, optionally mixed with a diblock copolymer S-(I/B) when the coupling efficiency is less than 100%, wherein S represents a predominantly poly(styrene) block, (I/B) represents a block of a randomly copolymerized mixture of predominantly isoprene and butadiene, wherein the weight ratio of isoprene to butadiene is in the range of from about 70:30 to about 30:70, (or in a mole/mole ratio of from about 1.1/0.55 to about 0.45/1.3) and wherein n is an integer in the range of from 3 to 5, preferably from 3 or 4, and X is the remainder of a coupling agent to be further specified hereinafter.

Preferred weight ratios of isoprene to butadiene are in the range of from about 60:40 to about 40:60 (or in a molar ratio of from about 0.89/0.75 to about 0.75/0.89). More preferably, the weight ratios of isoprene to butadiene are in the range of from about 55:45 to about 45:55.

As used herein, the terms "predominantly poly(styrene)" and "mixtures of predominantly isoprene and butadiene" mean that in addition to the main monomer, i.e. styrene on the one hand and on the other hand isoprene and butadiene, one or more other minor co-monomers may be present in the starting monomer in small amounts, i.e. up to about 5 wt % of co-polymerizable monomer. However, preferably substantially pure (co)monomers may be used for the preparation of the respective blocks. Examples of minor co-monomers, used in addition to styrene, include, but are not limited to alpha-methylstyrene, p-methylstyrene, o-methylstyrene, p-tert-butylstyrene, dimethylstyrene, vinyltoluene, vinylxylene, diphenylethylene and vinyl naphthalene or mixtures thereof.

The mixed polymer midblock (I/B) is made of butadiene and isoprene as copolymerizing monomers, although it may also contain minor amounts of other co-monomers, e.g. up to about 5 wt % of a co-polymerizable monomer such as styrene (based on the weight of the total block), but mixtures of substantially pure isoprene and butadiene are preferred.

In the block copolymers according to the present invention, the poly(styrene) content (which may include optional co-monomers) is in the range of from about 28 to about 50 wt %, preferably from about 28 to about 35 wt %, even more preferably from about 29 to about 33 wt %, based on the total block copolymer. The proportion of bound butadiene is from about 18 to about 80 wt %, preferably from about 40 to about 70 wt % in total. The proportion of bound isoprene is from about 15 to about 70 wt %, preferably from about 30 to about 70 wt %. These amounts of bound monomers (plus co-polymerizable monomers, if any) add up to 100 wt %.

The polymer blocks S preferably have a true molecular weight in the range from about 9,500 to about 25,000, more preferably from about 11,000 to about 16,000.

The block copolymers to be applied in the adhesive compositions according to the present invention preferably have a weight average molecular weight (Mw, expressed in terms of polystyrene) ranging from about 250,000 to about 500,000, more preferably from about 150,000 to about 230,000, as determined by gel permeation chromatography (GPC, using the method described by RUNYON, James R. et al. Multiple detectors for molecular weight and composition analysis of copolymers gel permeation chromatography. (*Journal of Applied Polymer Science*. 1969, vol.13, no. 11, p.2359-69)).

The block copolymers have a melt flow index measured at 200° C./5 kg ranging from about 1.0 to about 12 g/10 min.

The block copolymers to be applied in the adhesive compositions according to the present invention each preferably contain 1,2-vinyl bonds and/or 3,4-vinyl bonds in a proportion in the range of from about 4 to about 10 wt %, based on the weight of the conjugated diene, (or in the range of from about 0.08 to about 0.70 mole/mole %).

Preferably the (I/B) block has a vinyl content in the polymerized butadiene in the range of from about 7 to about 12 wt % and a vinyl content in the polymerized isoprene in the range of from about 4 to about 8 wt %. Even more preferably the (I/B) block has a vinyl content in the polymerized butadiene in the range of from about 7 to about 9 wt % and a vinyl content in the polymerized isoprene in the range of from about 4 to about 6 wt %.

Said block copolymers to be applied as main component (a) in the adhesive composition, have a randomly copolymerized block (I/B), which means that the mixed midblock shows no significant single homopolymer block formation. Such block copolymers can be prepared by a variety of methods such as that described in WO 02057386.

The block copolymers according to the present invention can be made e.g. by coupling living diblock copolymer prepared by anionic polymerization with a coupling agent. The coupling agent, can be tin coupling agents such as methyltin trichloride, tin tetrachloride; halogenated silicon coupling agents such as silicon tetrachloride and silicon tetrabromide; alkoxysilanes such as tetramethoxysilane; and halogenated alkanes such as trichloroethane, trichloropropane and tribromopropane. Silicon tetrachloride, silicon tetrabromide, tetramethoxysilane or other tetra(alkoxy)silanes are preferred.

The main block copolymer in component (a) may hence comprise a mixture of the coupled polymer according to the general formulae $[S-(I/B)]_nX$ and of the intermediate diblock S-(I/B), e.g. in a weight ratio of from about 100/0 to about 20/80, and preferably from about 100/0 to about 80/20.

The main block copolymer component (a) can be made by mere adaptation of common processes used for the preparation of $[S-B]_nX$ type block copolymers and/or $[S-I]_nX$ type block copolymers, using a mixture of butadiene/isoprene instead. The important point in the preparation of the block copolymers to be used according to the present invention is to avoid homopolymer diene block formation to ensure the desired (I/B) ratio.

The tackifying resins to be used in the hot-melt adhesive compositions of the present invention can be selected from a great variety of resins known to be applicable in hot-melt adhesives. The resins can be selected from modified aliphatic hydrocarbon resins such as modified C5 hydrocarbon resins (C5/C9 resins), styrenated terpene resins, fully or partially hydrogenated C9 hydrocarbon resins, hydrogenated cycloalophatic hydrocarbon resins, hydrogenated aromatic modified cycloaliphatic hydrocarbon resins, and mixtures thereof.

Preferable examples of resins to be used as component (b) include, but are not limited to: water white hydrocarbon resins of the ESCOREZ® resin series, such as ESCOREZ® 5600, ESCOREZ® 5400, ESCOREZ® 5300 and the like, or hydrocarbon resins of the REGALITE® resin series such as REGALITE® 1090, REGALITE® 7100 and REGALITE® S-5100 resins and the like, or the ARKON® resin series, like ARKON® P and M resin.

Preferred solid tackifying resins will have Ring and Ball softening points in the range of from about 90° C. to about 105° C. and will have an aromatic H-NMR content from 0 to about 30%, preferably from 0 to about 12%.

In the hot-melt adhesive compositions of the present invention, component (b) is present in an amount from 250 to 300 parts by weight of tackifing resin per 100 parts by weight of block copolymer component (a). In the preferred adhesive compositions, component (b) is applied in amounts of from 250 to 280 parts by weight of tackifying resin per 100 parts by weight of block copolymer component (a).

Suitable plasticizers include predominantly plasticizing oils that are paraffinic or naphthenic in character (carbon aromatic distribution ≦5%, preferably ≦2%, more preferably 0% as determined according to DIN 51378) and a glass transition temperature lower than −55° C. as measured by Differential Scanning Calorimetry. Those products are commercially available from the Royal Dutch/Shell Group of companies, such as SHELLFLEX®, CATENEX®, and ONDINA® oils. Other oils include KAYDOL® oil from Witco, TUFFLO® oils from Arco, NYPLAST® from NYNAS or CALSOL® 5555 from CALUMET LUBRICANTS. Other plasticizers include compatible liquid tackifying resins like REGALREZ® R-1018 or WINGTACK® 10.

Other plasticizers may also be added, such as olefin oligomers; low molecular weight polymers (≦30,000 g/mol) such as liquid polybutene, liquid polyisoprene copolymers, liquid styrene/isoprene copolymers or liquid hydrogenated styrene/conjugated diene copolymers; vegetable oils and their derivatives; or paraffin and microcrystalline waxes.

The hot-melt adhesive composition according to the present invention comprises a plasticizer in a weight proportion of from about 10 to about 30 wt %, relative to the weight of the complete composition and of from 50 to 150 parts by weight of plasticizer per 100 parts by weight of block copolymer constituent (a). Preferably the hot-melt adhesive composition comprises from 100 to 125 parts by weight of plasticizer per 100 parts by weight of block copolymer.

It will be appreciated that each block copolymer of component (a) may be pre-blended with a small amount of plasticizer by the manufacturer of said copolymer.

A variety of other rubber components may be incorporated into the adhesive compositions according to the present invention. It is also known in the art that various other components can be added to modify the tack, the odour, the color of the adhesives.

Antioxidants and other stabilizing ingredients such as endblock compatible resins like ENDEX® 160 can also be added to protect the adhesive from degradation induced by heat, light and processing or during storage. Several types of antioxidants can be used, either primary antioxidants like hindered phenols or secondary antioxidants like phosphite derivatives or blends thereof.

Examples of commercially available antioxidants include IRGANOX® 565 from Ciba-Geigy (2.4-bis-(n-octylthio)-6-(4-hydroxy-3,5-di-tertiary-butyl anilino)-1,3,5-triazine), IRGANOX® 1010 from Ciba-Geigy (tetrakis-ethylene-(3, 5-di-tertiary-butyl-4-hydroxy-hydrocinnamate)methane) and POLYGARD® HR from Uniroyal (tris-(2,4-di-tertiary-butyl-phenyl)phosphite). Other antioxidants developed to protect the gellling of the polybutadiene segments can also be used, such as SUMILIZER® GS from Sumitomo (2[1-(2-hydroxy-3,5-di-ter-pentylphenyl)ethyl)]-4,6-di-tert-pentylphenylacrylate); SUMILIZER® T-PD from Sumitomo (pentaerythrythyltetrakis(3-dodecylthiopropionate)); or mixtures thereof.

In the hot-melt adhesive compositions of the present invention, one or more stabilizers and/or antioxidants are optionally present. Accordingly, the one or more stabilizers and/or antioxidants are present in an amount from 0 to 3 parts by weight of stabililzers and/or antioxidants per 100 parts by weight of block copolymer component (a). In the preferred adhesive compositions, component (d) is applied in amounts of from 0.5 to 3, even more preferably from 0.5 to 2.5, parts by weight of component (d) per 100 parts by weight of block copolymer component (a).

No particular limitation is imposed on the preparation process of the adhesive composition. Therefore, any process may be used, such as a mechanically mixing process making use of rolls, a Banbury mixer or a Dalton kneader, a hot-melt process characterized in that heating and mixing are conducted by using a melting kettle equipped with a stirrer, such as a turbo-mixer, a high shear Z-blade mixer or a single- or twin-screw extruder, or a solvent process in which the compounding components are poured in a suitable solvent and stirred, thereby obtaining an intimate solution of the pressure sensitive adhesive composition.

Hot-melt adhesive compositions according to the present invention are efficiently applied as assembly adhesive composition or as attachment adhesive composition for assembling sanitary articles, in particular diapers, comprising a polyethylene framework and at least one non-woven lining element.

The following advantages of the formulated hot-melt adhesive compositions according to the present invention have been found:
  improved initial and heat-aged color;
  more resistance to viscosity changes;
  improved creep properties in elastic fiber adhesion; and
  good sprayability, even at high viscosities.

The following examples are provided to illustrate the present invention. The examples are not intended to limit the scope of the present invention and they should not be so interpreted.

EXAMPLES

The polystyrene content was determined by 1H-NMR.

The hot-melt viscosity was measured with a rotational viscometer following ASTM D-3236-78. The viscosity was measured by the torque required to rotate a spindle at constant speed while immersed in a fluid. The sample was placed in a RVTDV-II equipped with a Brookfield Thermocell and the hot-melt viscosity was measured in a temperature range of 110° C. to 160° C. The results were expressed in Pascal.second (Pa.s).

Synthesis of the Block Copolymers A to D

Cyclohexane, styrene, butadiene and isoprene were purified by activated aluminium oxide and stored at 4° C. under a nitrogen atmosphere. Prior to synthesis, a monomer mixture of butadiene and isoprene (at the weight/weight ratio given in Table 1) was prepared and stored under nitrogen at 4° C. This mixture was used as such.

An autoclave, equipped with a helical stirrer was charged with cyclohexane and the content was heated to 50 to 60° C. As initiator, sec-BuLi was dosed immediately followed by styrene monomer, which was allowed to polymerize to completion. The reaction temperature was increased to 70° C., at which temperature a butadiene/isoprene monomer mixture (B/I) was dosed and reacted. The resulting diblock was coupled with a coupling agent dosed at a stoichiometry typically less than ½ mole per mole of active polymer lithium chain-ends. This excess was optionally scavenged with sec-BuLi and followed by addition of ethanol to terminate the polymerization. The reaction mixture was cooled to 40° C., transported to a blending vessel and a stabilization package was added (comprising IRGANOX® 565 and IRGANOX® 168 0.08/0.35 phr as a cyclohexane solution) and stirred at room temperature. Dry rubber was obtained by steam coagulation finishing, followed by drying in an oven.

Table 1 lists the amounts in which the components (a) and (b) have been used. The polymers were analyzed by GPC and the results thereof are included in Table 2.

Polymers A, B and C were coupled with GPTS (3-GLYCIDOXYPROPYL)TRIMETHOXYSILANE) and have an average branching of about 3.2 arms. Polymer D was coupled with Epon 826 and has a linear structure. These polymers can also be polymerized with the hereinbefore described sequential/reinitiation technology.

TABLE 1

| | Polymer | | | |
|---|---|---|---|---|
| | A | B)* | C* | D |
| Cyclohexane (l) | 262.4 | 320.8 | 320.8 | 77 |
| Initiator (mmol) | 680.0 | 998.7 | 998.7 | 20.5 |
| Styrene (gram) | 9100 | 15230 | 15230 | 638 |
| B/I (ratio) | 60/40 | 1 | 1 | 1 |
| B/I (gram) | 21000 | 35220 | 35220 | 1490 |
| Epon 826 (gram) | | | | 0.24 |
| GPTS (gram) | 40.2 | 38.25 added to 126.4 kg cement | 23.98 added to 120.7 kg cement | |
| Ratio GPTS/Li | 0.25 | 0.29 | 0.23 | |

*Polymers B and C were made from a masterbatch of diblock then separated to make radial polymers of different coupling efficiency.

TABLE 2

| | Polymer | | | |
|---|---|---|---|---|
| | A | B | C | D |
| GPC $M_w$ Polystyrene * $10^3$ | 13.3 | 15.0 | 15.4 | 14.8 |
| GPC $M_w$ * $10^3$ | 152.7 | 200.3 | 190.1 | 134 |
| Coupling efficiency % | 75 | 78 | 66 | 81 |
| Polystyrene content wt % | 29.3 | 29.4 | 29.4 | 31 |
| Bd/Ip ratio wt/wt | 60/40 | 50/50 | 50/50 | 50/50 |
| Vinyl in Bd wt % | 10 | 9 | 9 | 9 |
| vinyl in Ip wt % | 6 | 6 | 6 | 6 |

Further components used in the tested adhesive compositions are as follows: VECTOR® 4211 from DEXCO is a linear styrene-isoprene-styrene block copolymer with 30% polystyrene content, a melt flow rate of 13 g/10 min and virtually no diblock content since the polymer was made sequentially.

Several tackifiers were used in the examples of the invention. ESCOREZ® 5600 is a hydrocarbon resin from EXXON MOBIL CHEMICAL. ESCOREZ® 5400 is a hydrocarbon resin from EXXON MOBIL CHEMICAL. CALSOL® 5555 is a naphthenic oil from CALUMET LUBRICANTS. ENDEX® 160 is a styrene block compatible resin from EASTMAN CHEMICAL. IRGANOX® 1010 is an antioxidant from CIBA.

The following hot-melt adhesive compositions, comprising the ingredients as specified hereinafter were composed as listed in Tables 3 and 5. Moreover, test results based on these formulations are presented in Tables 3-5.

TABLE 3

Viscosity and Peel Adhesion for Hot-Melt Adhesive Formulations

| | F1 | F2 | F3 | F4 | Benchmark* |
|---|---|---|---|---|---|
| Polymer D Linear | 20 | | | | |
| Polymer A | | 20 | | | |
| Polymer B | | | 20 | | |
| Polymer C | | | | 20 | |
| Escorez 5600 | 56.5 | 56.5 | 56.5 | 56.5 | |
| Calsol 5550 | 23 | 23 | 23 | 23 | |
| Irganox 1010 | 0.5 | 0.5 | 0.5 | 0.5 | |
| Viscosity @ 300 F. (cps) | 1480 | 3000 | 4790 | 5710 | 2960 |
| Spiral Peel Peak (grams) | 249 | 293 | 246 | 285 | 259 |
| Spiral Peel Average (grams) | 148 | 154 | 121 | 136 | 134 |

*Benchmark Formulation
20 phr SIS polymer (Dexco Vector ® 4211)
55.6 phr Escorez ® 5400
9 phr Endex ® 160
15 oil
0.4 Irganox ® 1010

To test thermal stability 300 grams of each adhesive was placed into a glass jar and conditioned at 300° F. for 96 hours. At 24 hour intervals, 10.5 grams was removed from each and checked for Gardner color and Brookfield viscosity at 300° F.

TABLE 4

Thermal Stability Data

| | F1 | F2 | F3 | F4 | Benchmark |
|---|---|---|---|---|---|
| Initial Viscosity @ 300° F. (cps) | 1480 | 3000 | 4790 | 5710 | 2960 |
| 24 hours | 1390 | 2520 | 4140 | 4940 | 2475 |
| 48 hours | 1160 | 1970 | 3170 | 4210 | 1660 |
| 72 hours | 985 | 1580 | 2810 | 3010 | 1130 |
| 96 hours | 910 | 1410 | 2150 | 2570 | 970 |
| % change | −38 | −53 | −55 | −55 | −67 |
| Initial Gardner Color | 2 | 1 | 1 | 1 | 3 |
| 24 hours | 3 | 2 | 1 | 2 | 3 |
| 48 hours | 4 | 3 | 2 | 2 | 4 |
| 72 hours | 5 | 4 | 2 | 3 | 5 |
| 96 hours | 6 | 5 | 3+ | 4+ | 5 |

To test elatic attachment 2000 gram batches of each adhesive were prepared in a high shear sigma blade mixer set at 325° F. The adhesives were then transferred to a melter set at 300° F. and applied with a Nordson spiral spray system onto three strands of Lycra thread using the method described in Werenicz U.S. Pat. No. 4,842,666. After equilibrating to room temperature, the laminations were then stretched to 95% of full extension and fastened to a rigid piece of cardboard. The ends of the elastic were then cut through the polyethylene film and the test board placed in an incubator set at 100° F. After a period of four hours, the test board was removed and the percent creep calculated using the formula: Initial length minus final length divided by initial length times 100.

TABLE 5

Elastic Attachment Viscosity and % Creep Data

| | F1 | F2 | F3 | F4 | Comparison* |
|---|---|---|---|---|---|
| Polymer D Linear | 23 | | | | |
| Polymer A | | 23 | | | |
| Polymer B | | | 23 | | |
| Polymer C | | | | 23 | |

TABLE 5-continued

Elastic Attachment Viscosity and % Creep Data

|  | F1 | F2 | F3 | F4 | Comparison* |
|---|---|---|---|---|---|
| Escorez ® 5400 | 56.5 | 56.5 | 56.5 | 56.5 |  |
| Calsol ® 5550 | 13 | 13 | 13 | 13 |  |
| Endex ® 160 | 7 | 7 | 7 | 7 |  |
| Irganox ® 1010 | 0.5 | 0.5 | 0.5 | 0.5 |  |
| Brookfield viscosity @ 300° F. (cps) | 4940 | 9350 | 13900 | 13900 | 5725 |
| % creep | 16.8 | 13.3 | 11.6 | 13 | 12.3 |
| Lycra XA-940 (% stretch) | 300 | 300 | 300 | 300 | 300 |

*Comparison Formulation
20 phr SIS polymer (Dexco Vector ® 4211)
55.6 phr Escorez ® 5400
9 phr Endex ® 160
15 oil
0.4 Irganox ® 1010

Compared to the SIS radial polymer comparison, both the linear and the radial mixed mid-block polymers of the present invention had excellent resistance to viscosity degradation. The radial polymers showed superior color stability which is an important property in non-woven article manufacturing. For elastic attachment to Lycra XA-940, the radial polymers A-C showed superior creep properties compared to the linear versions. One unanticipated result was that even at very high viscosity, the radial mixed-midblock polymers had excellent sprayability. This is an important feature of the radial mixed-midblock polymers and allows a wider formulation window.

What is claimed is:

1. A hot-melt adhesive composition used in non-woven assemblies, comprising
   (a) 100 parts by weight of a block copolymer of the formula $[S-(I/B)]_n X$, wherein S represents a predominantly poly(styrene) block and (I/B) represents a polymer block obtained by a random copolymerization of a mixture of predominantly isoprene and butadiene in a weight ratio in the range of from 70:30 to 30:70, wherein n is an integer in the range of from 3 to 5, and wherein X is the remainder of a coupling agent, wherein the block copolymer has a poly(styrene) content of from 28 to 50 wt % and a coupling efficiency of from 50 to 100%, and a melt flow index measured at 200° C./5 kg ranging from 1.0 to 12 g/10 min,
   (b) from 250 to 300 parts by weight of a tackifying resin,
   (c) from 50 to 150 parts by weight of a plasticizer, and
   (d) from 0 to 3 parts by weight of one or more stabilizers and/or antioxidants.

2. The adhesive composition of claim 1, wherein the block (I/B) has been obtained by a random polymerization of a mixture of butadiene and isoprene in a weight ratio of from 60:40 to 40:60.

3. The adhesive composition of claim 1, wherein the block (I/B) has been obtained by a random polymerization of a mixture of butadiene and isoprene in a weight ratio of from 55:45 to 45:55.

4. The adhesive composition of claim 2, wherein the (I/B) block has a vinyl content in the polymerized butadiene in the range of from 7 to 12 wt % and a vinyl content in the polymerized isoprene in the range of from 4 to 8 wt %.

5. The adhesive composition of claim 1, wherein the (I/B) block, has a vinyl content in the polymerized butadiene in the range of from 7 to 9 wt % and a vinyl content in the polymerized isoprene in the range of from 4 to 6 wt %.

6. The adhesive composition of claim 4, wherein the block copolymer S-(I/B)-S has a polystyrene content of from 28 to 35 wt %.

7. The adhesive composition of claim 1, wherein the block copolymer S-(I/B)-S has a polystyrene content of from 29 to 33 wt %.

8. The adhesive composition of claim 1, wherein from 250 to 280 parts by weight of hydrocarbon resin per 100 parts by weight of block copolymer have been included.

9. The adhesive composition of claim 1, wherein the coupling efficiency of the block copolymer $[S-(I/B)]_n X$ is from 50 to 85%.

10. The adhesive composition of claim 6, wherein the coupling efficiency of the block copolymer $[S-(I/B)]_n X$ is from 50 to 85%.

11. The adhesive composition of claim 10, wherein the one or more stabilizers and/or antioxidants are present in an amount from 0.5 to 3 parts by weight.

12. A disposable article selected from the group consisting of infant and adult diapers or sanitary napkins, incontinent pads, bed pads, feminine pads, and panty shields, comprising at least one non-woven element and assembled by the use of the hot-melt adhesive comprising
   (a) 100 parts by weight of a block copolymer of the formula $[S-(I/B)]_n X$, wherein S represents a predominantly poly(styrene) block and (I/B) represents a polymer block obtained by a random copolymerization of a mixture of predominantly isoprene and butadiene in a weight ratio in the range of from 70:30 to 30:70, wherein n is an integer in the range of from 3 to 5, and wherein X is the remainder of a coupling agent, wherein the block copolymer has a poly(styrene) content of from 28 to 50 wt % and a coupling efficiency of from 50 to 100%, and a melt flow index measured at 200° C./5 kg ranging from 1.0 to 12 g/10 min,
   (b) from 250 to 300 parts by weight of a tackifying resin,
   (c) from 50 to 150 parts by weight of a plasticizer, and
   (d) from 0 to 3 parts by weight of one or more stabilizers and/or antioxidants.

13. A block copolymer of the formula $[S-(I/B)]_n X$ wherein S represents a predominantly poly(styrene) block and (I/B) represents a polymer block obtained by a random copolymerization of a mixture of predominantly isoprene and butadiene in a weight ratio in the range of from 60:40 to 40:60, wherein n is an integer in the range of from 3 to 5, wherein X is the residue of a coupling agent and wherein the total block copolymer has a melt flow index measured at 200° C./5 kg in the range of from 1.0 to 12 g/10 min., and has a poly(styrene content of from 28 to 50 wt % and a coupling efficiency of from 50 to 100%.

14. The block copolymer of claim 13, wherein the S blocks have been derived from substantially pure styrene.

15. The block copolymer of claim 14, wherein the (I/B) block has a vinyl content in the polymerized butadiene in the range of from 7 to 12 wt % and a vinyl content in the polymerized isoprene in the range of from 4 to 8 wt %.

16. The block copolymer of claim 13, wherein the (I/B) block has a vinyl content in the polymerized butadiene in the range of from 7 to 9 wt % and a vinyl content in the polymerized isoprene in the range of from 4 to 6 wt %.

17. The block copolymer of claim 15, wherein the block copolymer [S-(I/B)]$_n$X has a polystyrene content of from 28 to 35 wt %.

18. The block copolymer of claim 13, wherein the block copolymer [S-(I/B)]$_n$X has a polystyrene content of from 28 to 35 wt %.

19. The block copolymer of claim 13, wherein the block copolymer [S-(I/B)]$_n$X has a coupling efficiency of from 50 to 85%.

20. The block copolymer of claim 17, wherein the block copolymer [S-(I/B)]$_n$X has a coupling efficiency of from 50 to 85%.

* * * * *